(12) United States Patent
Gitis et al.

(10) Patent No.: US 6,418,776 B1
(45) Date of Patent: Jul. 16, 2002

(54) METHOD AND APPARATUS FOR MEASURING FRICTION AND WEAR CHARACTERISTICS OF MATERIALS

(75) Inventors: Norm Gitis, Cupertino; Michael Vinogradov; Vlad Dorfman, both of Sunnyvale, all of CA (US)

(73) Assignee: Center for Tribology, Inc., Campbell, CA (US)

(*) Notice: Subject to any disclaimer, the term of this patent is extended or adjusted under 35 U.S.C. 154(b) by 0 days.

(21) Appl. No.: 09/624,500

(22) Filed: Jul. 24, 2000

(51) Int. Cl.[7] ................................................. G01N 3/56
(52) U.S. Cl. ................................................. 73/10; 73/9
(58) Field of Search ...................................... 73/7, 9, 10

(56) References Cited

U.S. PATENT DOCUMENTS

| | | | |
|---|---|---|---|
| 4,448,083 A | * | 5/1984 | Hayashi ................. 73/862.042 |
| 4,939,922 A | * | 7/1990 | Smalley et al. ................. 73/10 |
| 5,795,990 A | | 8/1998 | Gitis et al. |
| 6,167,745 B1 | * | 1/2001 | Hamer et al. ..................... 73/9 |

* cited by examiner

*Primary Examiner*—Robert Roers Raevis
(74) *Attorney, Agent, or Firm*—Ilya Zborovsky (57) ABSTRACT

A universal friction tester for testing tribological properties of materials comprises a frame with a carriage sliding in vertical guides and supporting a slide moveable in a horizontal direction. The slide supports a stationary upper specimen, which engages a moveable lower specimen, located in a replaceable module attachable to a base plate of the frame. The modules may be of a rotary, reciprocating, a block-on-ring, or any other type, required for different test conditions. Testing can also be carried out with heating or with the supply of oil in the zone of contact between the specimens.

20 Claims, 10 Drawing Sheets

METHOD AND APPARATUS FOR MEASURING FRICTION AND WEAR CHARACTERISTICS OF MATERIALS

FIELD OF THE INVENTION

The present invention relates to the field of tribology and, more particularly, to a method and apparatus for testing and measuring friction, wear characteristics of materials, and tribological properties of lubricants.

BACKGROUND OF THE INVENTION

Figure 1:
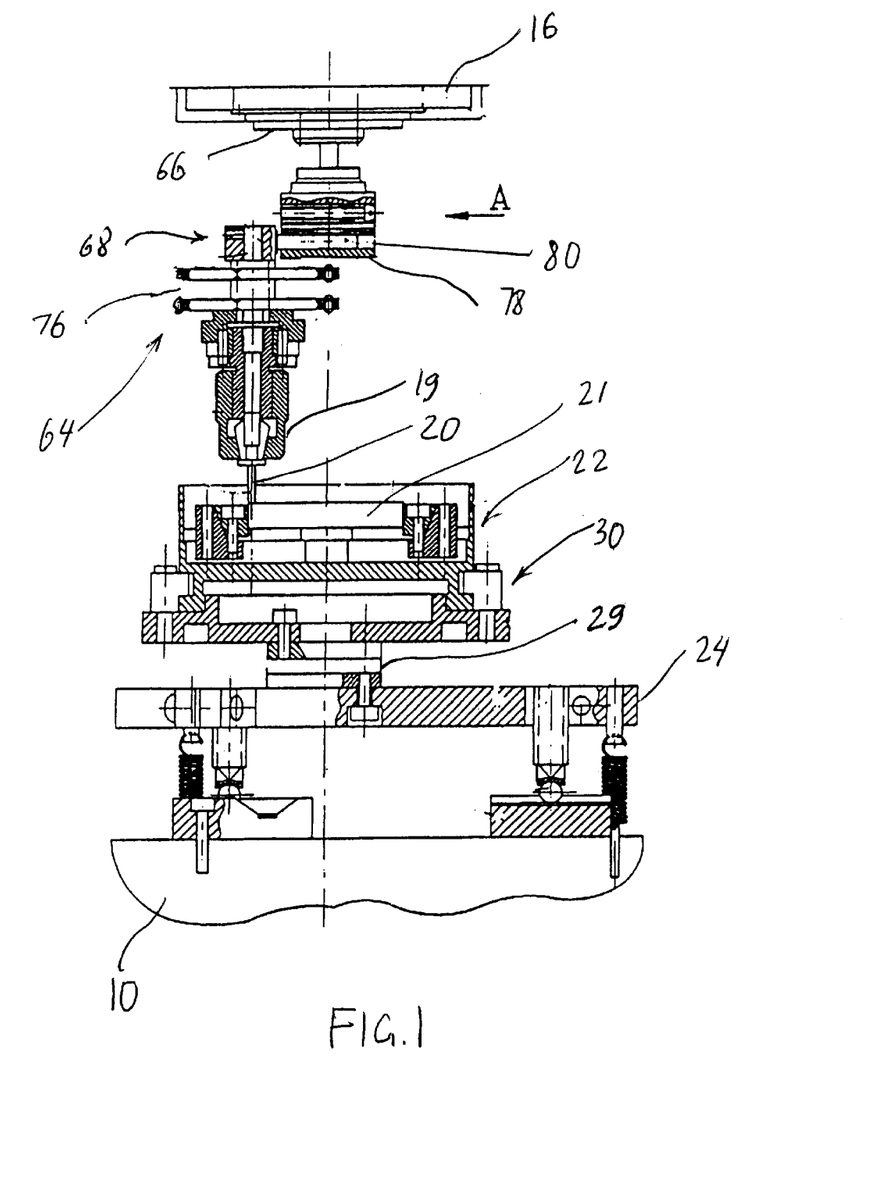
FIG. 1 is a fragmental sectional view of a known friction tester for measuring friction and wear characteristics of the materials and lubricants.

Tribology is a science of friction, wear, and lubrication on friction surfaces. Many different types of friction testers, tribometers, and other devices for measuring various parameters of friction are known. U.S. Pat. No. 5,795,990 issued in 1998 to N. Gitis, et al. describes a friction tester which has a horizontal base with a vertical column that supports vertical guides for guiding a carriage. FIG. 1 is a fragmental sectional view of the aforementioned tester, which has a lower base 10, and a vertical column (not shown). A carriage 16 supports a rotary stepper motor (not shown) that rotates an upper specimen holder 64 via a reducer 66. The upper specimen holder 64 is strictly coaxial with the center of a bowl 22, which is supported by the lower base 10 via a lower plate 24. The upper specimen holder 64 has a radial guiding slot, which serves for guiding a slider 68, the position of which can be adjusted by means of a micrometric screw. The upper specimen holder 64 supports a collet chuck 19 that holds an upper specimen 20 by means of a coupling 76 supported in the upper specimen holder 64 by means of an angular adapter 78 which has a horizontal axle 80 inserted into an opening of the slider 68.

A sensor, e.g., a load cell 29, is placed between the lower plate 24 and an intermediate plate 30 for measuring a friction force and friction torque developed during testing between the upper specimen 20 and a lower specimen 21.

Thus, in the known tester of U.S. Pat. No. 5,795,990, the slider and the collet chuck 19 together with the upper specimen 20 perform orbital movements over the stationary lower specimen 21. Rotation of these relatively heavy parts develops centrifugal forces which deform, i.e., bends, the rotating chuck 19 with the upper specimen 20 radially outwardly from the vertical axis of rotation. It is impossible to obtain accurate measurements and it is difficult to provide electrical connections with the rotating parts, e.g., if a heater is installed on a rotating part. Furthermore, the orbital rotation of aforementioned heavy parts limits frequency of rotation (which did not exceed 60 rpm in a real tester) and requires the use of the reducer 66 (which was a harmonic drive reducer in a real tester).

Another disadvantage of the known tester is lack of versatility resulting from the upper attachment of the rotating parts. Such an arrangement limits a space for attachment of various replaceable modules, such as modules with heating, reciprocating drives, etc.

In the known tester the sensor 29 is located beneath the bowl 22 and all other fixtures, so that the weight of these devices acts on the sensor and therefore does not allow obtaining accurate measurements.

OBJECTS OF THE INVENTION

It is an object of the present invention to provide an apparatus for testing and measuring tribological properties of the materials and lubricants which is simple in construction, reliable in operation, universal in use, allows testing with high frequencies of rotation and under different temperatures, prevents deformations in the friction force measurement system, and therefore ensures accurate measurements. Another object of the invention is to provide a method for testing and measuring tribological properties of the materials and lubricant which is reliable and allows testing in a wide range of operation conditions.

SUMMARY OF THE INVENTION

A universal friction tester for testing tribological properties of materials comprises a frame with a carriage sliding in vertical guides and supporting a slide moveable in a horizontal direction. The slide supports a stationary upper specimen, which engages a moveable lower specimen, located in a replaceable module attachable to a base plate of the frame. The modules may be of a rotary, reciprocating, a block-on-ring, or any other type, required for different test conditions. Testing can also be carried out with heating or with the supply of oil in the zone of contact between the specimens.

DETAILED DESCRIPTION OF THE INVENTION

Figure 2:
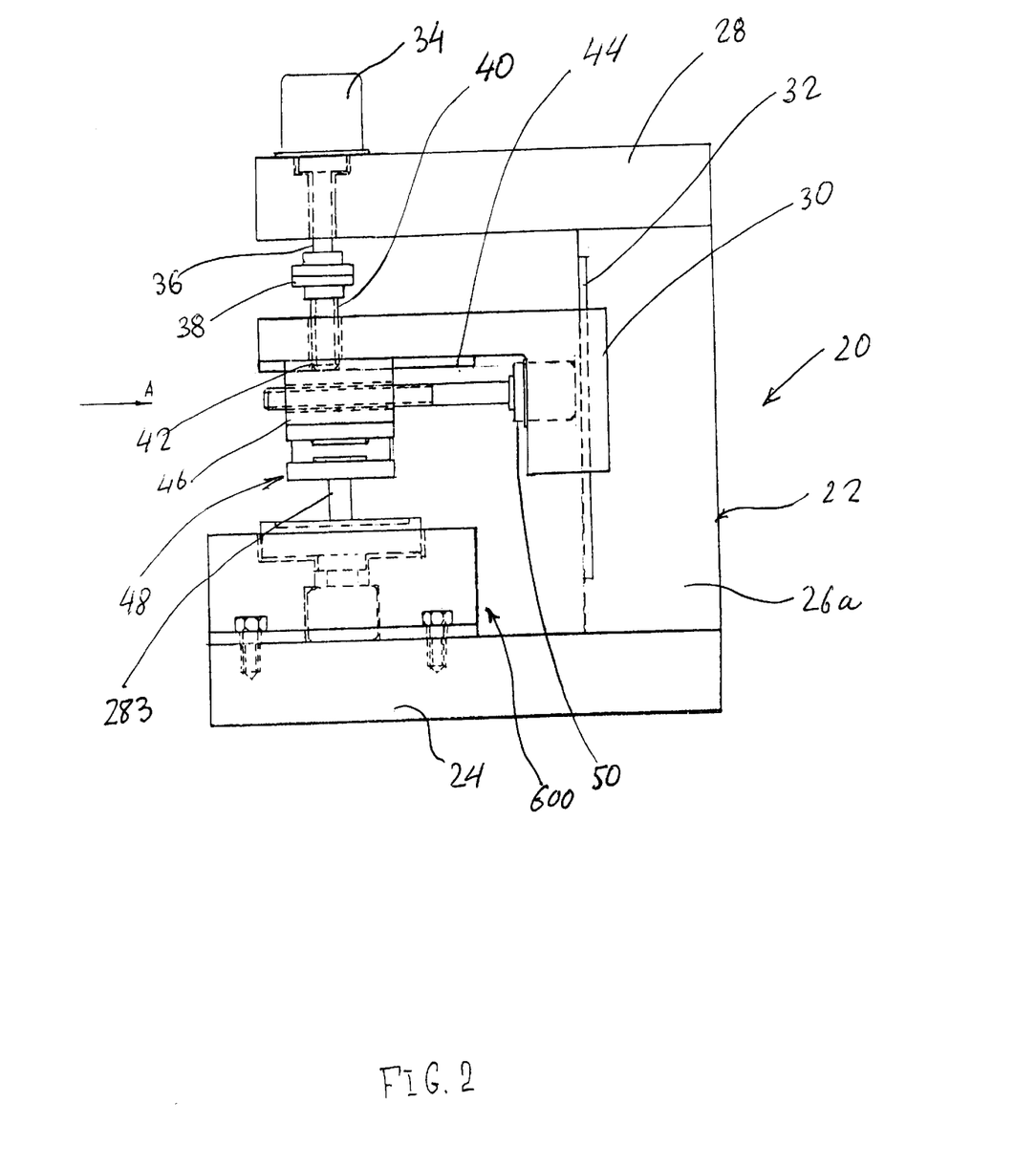
FIG. 2 is a side view of a friction tester of the present invention.
Figure 3:
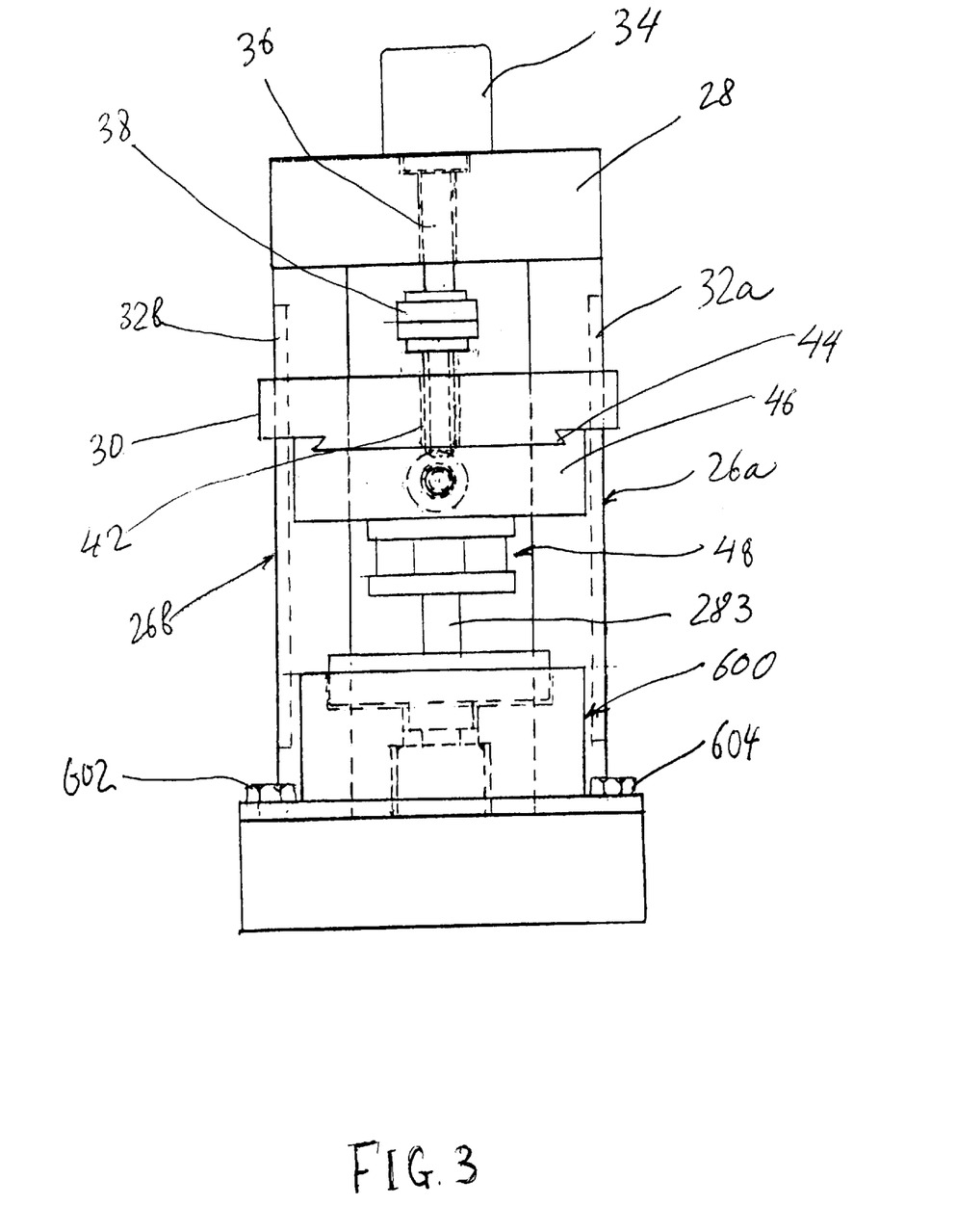
FIG. 3 is a view of the friction tester of the invention in the direction of arrow A in FIG. 2.

A friction tester of the present invention is shown as a whole in FIGS. 2 and 3, where FIG. 2 is a side view of a friction tester of the present invention, and FIG. 3 is a view of the friction tester in the direction of arrow A in FIG. 2.

As can be seen from these drawings, the tester, which in general is designated by reference numeral 20, has a frame 22 consisting of a base plate 24, a vertical columns 26a, 26b and a cross bar 28. The vertical columns 26a, 26b slidingly support a carriage 30. moveable in slides 32a, 32b and driven by a reversible electric motor 34 supported by the cross bar 28. For that purpose, an output shaft 36 of the motor 34 is connected via a coupling 38 to a lead screw 40 which is in engagement with a thread of a threaded hole 42 formed in the carriage 30. Thus, rotation of the motor 34 causes movement of the carriage in a vertical direction along the guides 32a, 32b.

The carriage 30, in turn, has a horizontal guide slot 44 (FIG. 3) for guiding a slide 46 which supports a sensor assembly 48 which is described in detail later. The slide is driven for movement in the horizontal direction in the guide slot 44 by a reversible electric motor 50 installed on a carriage 30.

Attached to the lower side of the slide 46 is a sensor assembly 48. As can be seen from FIG. 4, which is a three-dimensional exploded view of the sensor assembly 48, this device consists of a lower plate 102 of a rectangular shape, an upper plate 104 which has substantially the same shape and dimensions as the plate 102, and a pair of sensors 200 and 300 sandwiched between the lower plate 102 and the upper plate 104. The upper plate 104 is connected to the slide 46, and the lower plate supports a stationary upper specimen 283, which during testing is maintained in contact with a moveable lower specimen (not shown in FIG. 4). The specimens will be shown and described later in connection with operation of the device. Both sensors are spaced from each other and are arranged symmetrically opposite to each other. In other words, the sensor 200 is located in a position turned 180° with respect to the sensor 300.

Each sensor has a construction and function described in detail in U.S. patent application Ser. No. 6,324,918 filed by the same applicants on Dec. 4, 2001. Since both sensors 200 and 300 are identical, for better understanding the principle of the present invention, the description of one of the sensors, e.g., the sensor 200, will now be repeated.

Figure 4:
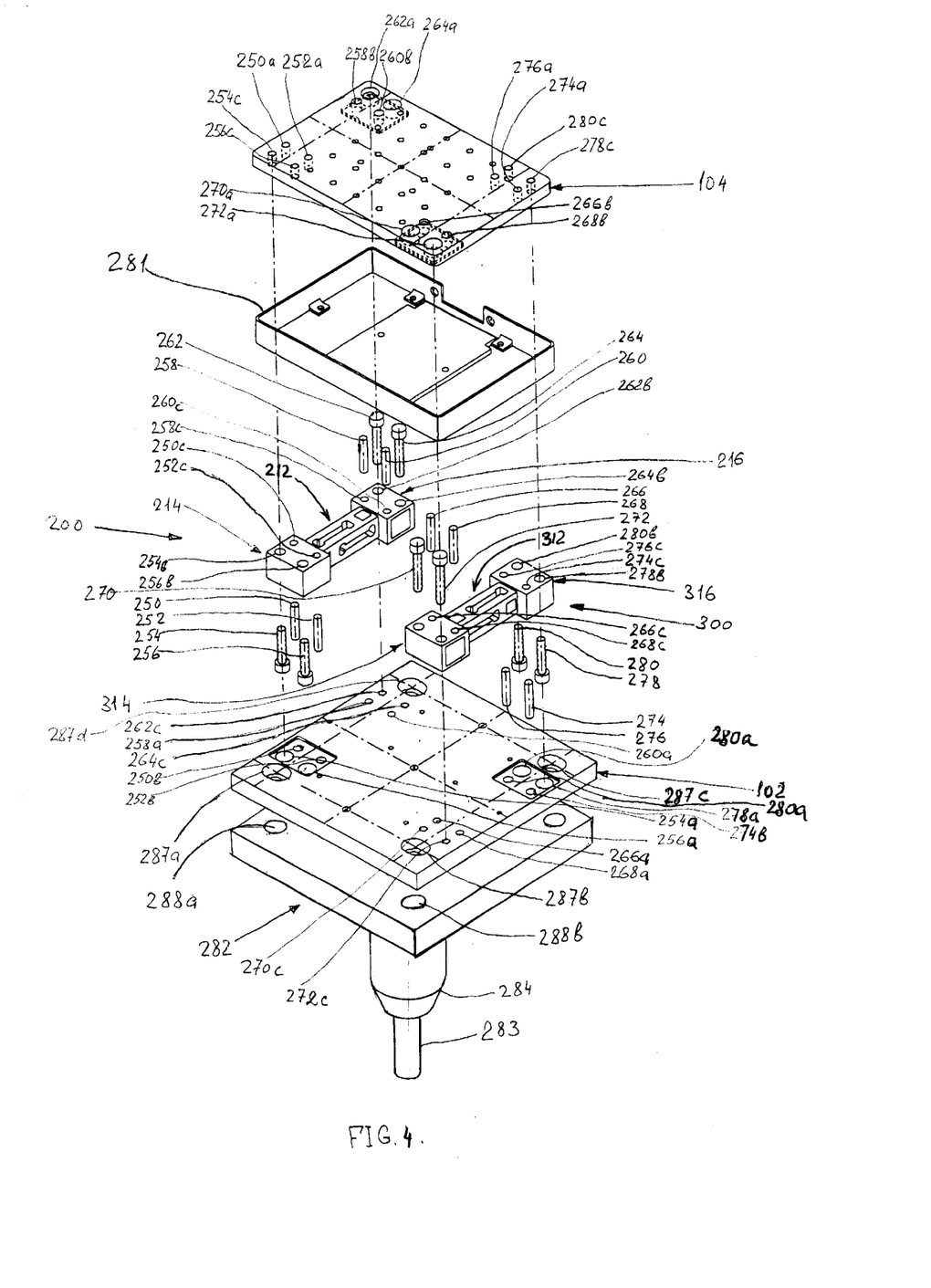
FIG. 4 is a three-dimensional exploded view of the sensor assembly used in the friction tester of invention.
Figure 5:
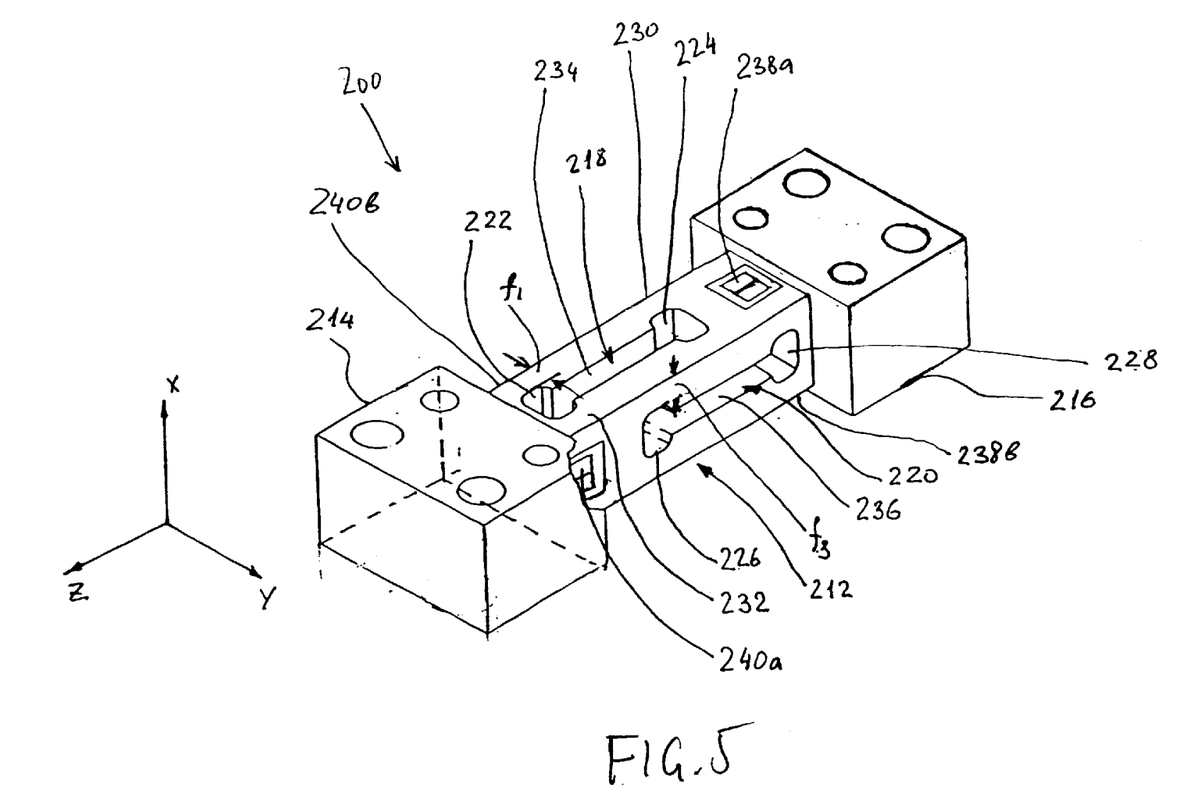
FIG. 5 is a three-dimensional view of one sensor used in the sensor assembly of FIG. 4.

FIG. 5 is a three-dimensional view of the sensor 200 used in the assembly of FIG. 4. The sensor comprises a flexible beam 212 of a rectangular cross section with rigid solid end blocks 214 and 216 at both ends for securing the sensor to the upper and lower plates 104 and 102, respectively (FIG. 4). The beam 212 has two symmetrically shaped through slots 218 and 220 cut in mutually perpendicular directions X and Y, respectively. The slots 218 and 220 partially intersect within a body of the beam 212. Each slot has on its opposite ends a through hole or notch, i.e., notches 222, 224 on the opposite ends of the slot 218 and through notches 226, 228 on the opposite ends of the slot 220, respectively. The notches 222, 224 and 226, 228 are wider than the respective slots 218 and 220.

The distances "$f_1$" and "$f_3$" from the inner walls of the respective notches 222 and 226 to the outer side surfaces 230 and 232 (only the edge of which is seen in FIG. 5) of the beam are shorter than the distances to the surface 230 and 232 from the inner walls 234 and 236 of the slots 218 and 220. The thinned portions of the beam 212 impart anisotropic flexibility to the beam required for increasing sensitivity of the sensor. The aforementioned anisotropic flexibility is ensured in the direction perpendicular to the direction of a respective slot and thus coincides with the direction of the force to be measured. In other words, for a force acting in the direction of axis X flexibility will be provided only in the direction of axis X by the notches 226 and 228 of the slot 220, and for a force acting in the direction of axis Y flexibility will be provided only in the direction of axis Y by the notches 222 and 224 of the slot 218.

In fact, the beam 212 with the slots 218 and 220 cut through the body of the beam in two different intersecting directions, which in the embodiment shown in FIG. 5 are two mutually perpendicular directions, can be compared with a pair of mutually overlapped parallelograms combined in one body which will be described later in connection with the operation of the sensor.

Force sensing elements, such as strain gauges 238a, 238b and strain gauges 240a, 240b are attached to mutually perpendicular surface areas at the ends of the beam which are flexible enough (due to provision of the notches) to comply with sensitivity of strain gauges used for measuring deformations and registering the measured deformations with appropriate electronic instrumentation (not shown). Similar pairs of strain gauges (not seen in FIG. 5) are attached to mutually perpendicular surface areas on the opposite sides of the beam.

The dimensions of the slots 218, 220 as well as the notches 222, 224 and 226, 228 are chosen in connection with the material of the beam so that deformations caused by the measured forces are reversible without residual deformations and directly proportional to the aforementioned forces. It is understood that the strain gauges 238a, 238b, 240a, 240b, etc., should be chosen so as to respond to mechanical deformations caused by measured forces within the entire possible range of the forces.

Examples of sensing elements suitable for the above purposes are strain gauges of N2AQ-XX-S061P-350 type produced by Measurement Group VISHAY, Raleigh, N.C., U.S.A. Such a sensing element normally comprises a thin-film serpentine-type resistor, which can be connected to one arm of a bridge-type or a potentiometric electric measurement circuit.

The sensor 300 is identical to the aforementioned sensor 200. Therefore only end blocks 314, 316 and a beam 312 of the sensor 300 are designated in FIG. 4.

The end block 214 of the sensor 200 is positioned with respect to the upper plate 104 by means of set pins 250 and 252 inserted into openings 250a and 252a of the upper plate 104 through openings 250b and 252b of the lower plate 102 and openings 250c and 252c of the end block 214. The end block 214 is attached to the upper plate 104 by means of bolts 254 and 256 inserted through openings 254a and 256a of the lower plate 102, openings 254b, 256b of the end block 214, and screwed into threaded openings 254c, 256c of the upper plate 104.

The end block 216 of the sensor 200 is positioned with respect to the lower plate 102 by means of set pins 258 and 260 inserted into openings 258a and 260a of the lower plate 102 through openings 258b and 260b of the upper plate 104 and openings 258c and 260c of the end block 216. The end block 216 is attached to the lower plate 102 by means of bolts 262 and 264 inserted through openings 262a and 264a of the upper plate 104, openings 262b, 264b of the end block 216, and screwed into threaded openings 262c, 264c of the lower plate 102.

The end block 314 of the sensor 300 is positioned with respect to the lower plate 102 by means of set pins 266 and 268 inserted into openings 266a and 268a of the lower plate 102 through openings 266b and 268b of the upper plate 104 and openings 266c and 268c of the end block 314. The end block 314 is attached to the lower plate 102 by means of bolts 270 and 272 inserted through openings 270a and 272a of the upper plate 104, openings 270b, 272b of the end block 314, and screwed into threaded openings 270c, 272c of the lower plate 102.

The end block 316 of the sensor 300 is positioned with respect to the upper plate 104 by means of set pins 274 and 276 inserted into openings 274a and 276a of the upper plate 104 through openings 274b and 276b of the lower plate 102 and openings 274c and 276c of the end block 316. The end block 316 is attached to the upper plate 104 by means of bolts 278 and 280 inserted through openings 278a and 280a of the lower plate 102, openings 278b, 280b of the end block 316, and screwed into threaded openings 278c, 280c of the upper plate 104.

Figure 6:
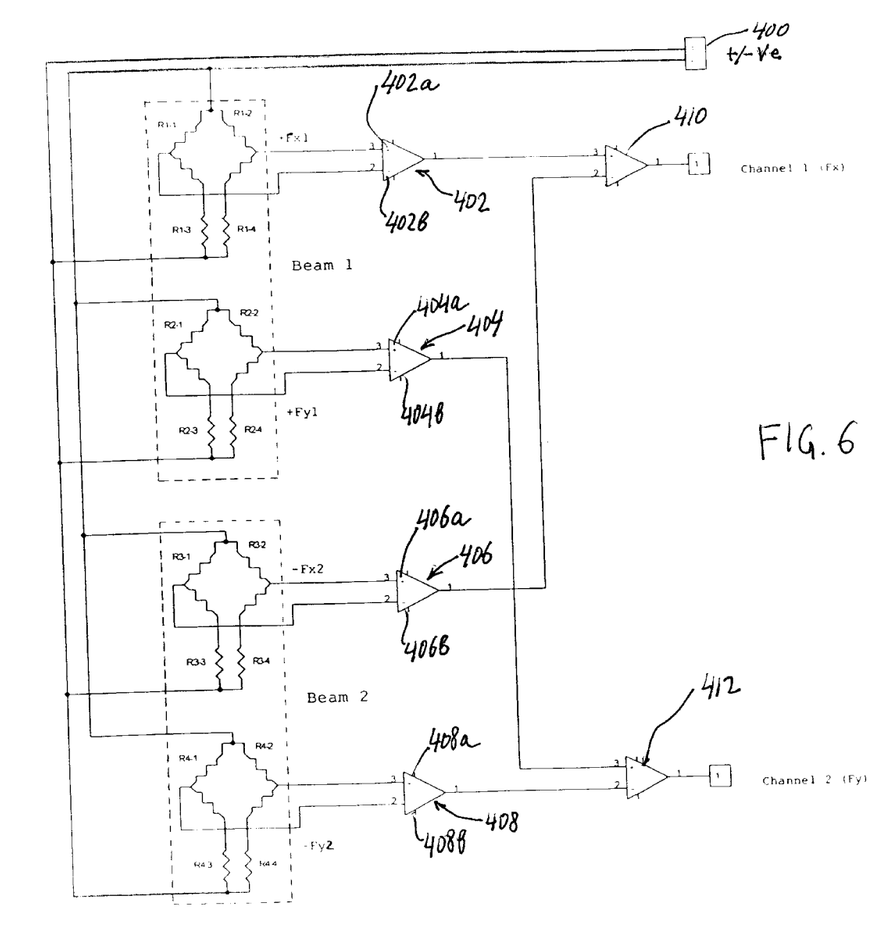
FIG. 6 is an example of an electric circuit for connection of double-force sensors to the registration measurement apparatus.

An example of a bridge-type connection circuit for strain gauges 238a, 238b, 240a, 240b, etc., is shown in FIG. 6. In this circuit, R1-1 designates a pair of resistors corresponding to the strain gauges 238a of the sensor 200 shown in FIG. 5, whereas R1-2 designates a pair of resistors corresponding to the strain gauges 238b which are located on the side of the sensor 200 opposite to the side of the strain gauges 238a and which are not seen in the drawing. The pairs of resistors R1-1 and R1-2 form a first bridge. R1-3 and R1-4 designate balancing resistors for the first bridge. R2-1 designates a pair of resistors corresponding to the strain gauges 240a of the sensor 200 shown in FIG. 5, whereas R2-2 designates a pair of resistors corresponding to the strain gauges 240b which are located on the side of the sensor 200 opposite to the side of the strain gauges 240a and which are not seen in the drawing. The pairs of resistors R2-1 and R2-2 form a second bridge. Resistors R2-3 and R2-4 are balancing resistors for the second bridge.

R3-1 and R3-2 designate pairs of resistors, which form a third bridge and which are located on the sensor 300 similarly to the pairs of resistors R1-1 and R1-2 of the beam 200. R3-3 and R3-4 are balancing resistors of the third bridge. R4-1 and R4-2 designate pairs of resistors, which form a fourth bridge and which are located on the sensor 300 similarly to the pairs of resistors R2-1 and R2-2 of the sensor 300. R4-3 and R4-4 are balancing resistors for the fourth bridge.

In the electric circuit of FIG. 6, reference numeral 400 designates a power source, which is connected to each bridge formed by respective strain gauges and balancing resistors in both sensors 200 and 300. As shown in FIG. 6, both output leads of the first bridge formed by the resistors R1-1 and R1-2 are connected to a positive and a negative inputs 402a and 402b, respectively, of the first adding amplifier 402. Similarly, both output leads of the second bridge formed by the resistors R2-1 and R2-2 are connected to a positive and negative inputs 404a and 404b, respectively, of the second adding amplifier 404.

Similarly, both outputs of the third bridge formed by the resistors R3-1 and R3-2 are connected to positive and negative inputs 406a and 406b, respectively, of the third adding amplifier 406. Both outputs of the fourth bridge formed by the resistors R4-1 and R4-2 are connected to a positive and negative inputs 408a and 408b, respectively, of the fourth adding amplifier 408.

Outputs of the first amplifier 402 and of the third amplifier 406, which produce output signals corresponding to force $F_x$ acting in the direction of axis X and measured by both sensors 200 and 300, respectively, are supplied to a first output amplifier, whereas outputs of the second amplifier 404 and of the fourth amplifier 408, which produce output signals corresponding to force $F_y$ acting in the direction of axis Y and measured by both sensors 200 and 300, respectively, are supplied to a second output amplifier 412.

An output of the amplifier 410 is connected to channel 1 and an output of amplifier 412 is connected to channel 2 of the measurement and registration apparatus (not shown).

Attached to the lower plate 102 is a specimen mounting plate 282 for attaching an upper specimen 283 which is secured in a chuck 284 connected to mounting plate 282 by bolts 285a, 285b, 285c. Mounting plate 282 is connected to lower plate 102 by bolts 286a, 286b, 286c, and 286d which are screwed into threaded opening 287a, 287b, 287c, and 287d of the lower plate 102 via openings 288a, 288b, 288c, 288d. The positioning is achieved by means of set screws 289a, 289b. The upper specimen 283 is located in the geometrical center of the lower plate. It is assumed that the loading force F is applied to this point.

Attached to the base plate 24 is a replaceable lower-specimen module 600 (FIGS. 2 and 3) which is attached, e.g., by bolts 602, 604 and may be a module of any type, such as rotary, reciprocating, block-on-ring, etc. Several examples of such modules will be given below. However, a common feature of all lower-specimen modules is that all of them are provided with a drive unit intended for moving the lower specimen relative to a stationary upper specimen 283. This drive can be rotary or reciprocating, and the lower specimen can be tested with heating, or in an oil bath.

Figure 7:
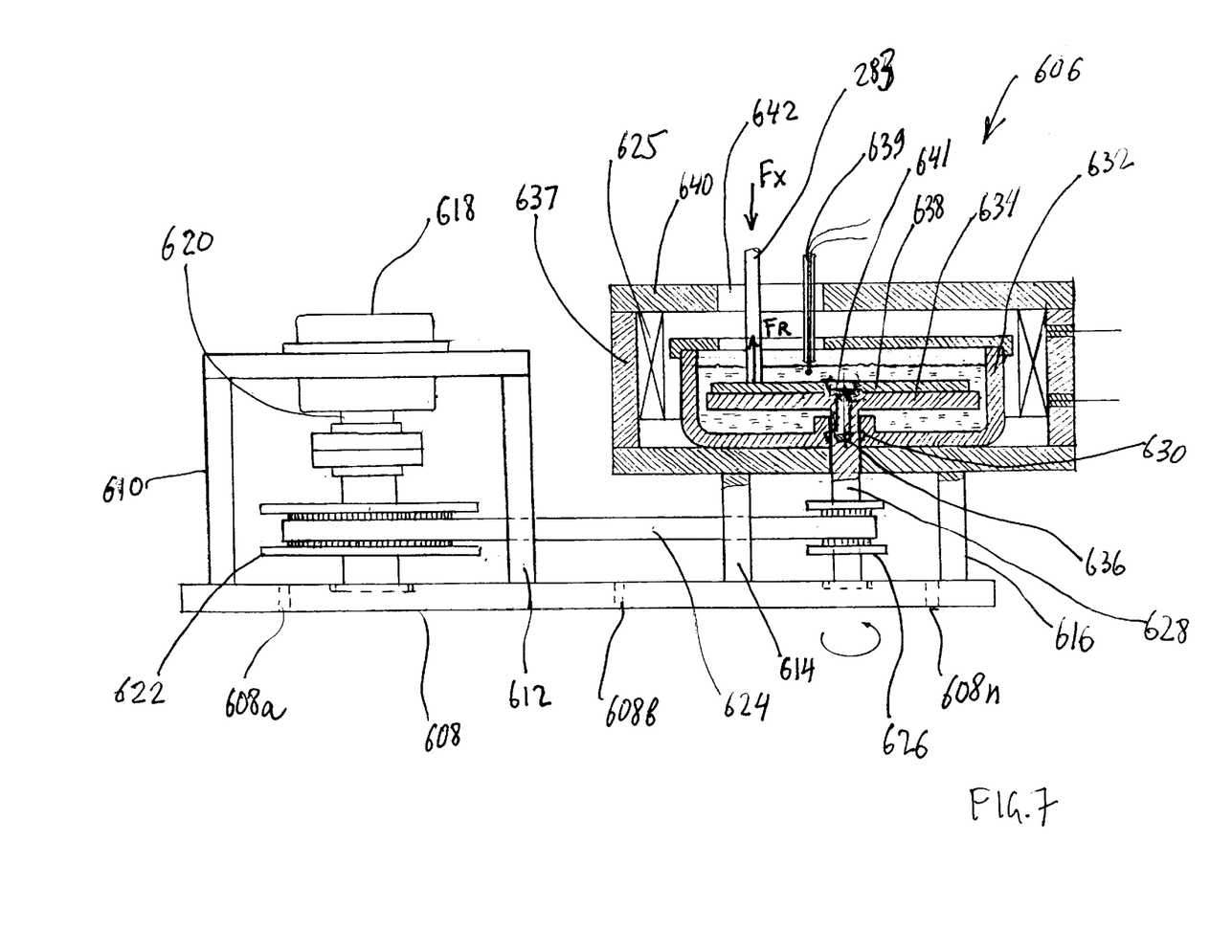
FIG. 7 is a view of an interchangeable lower-specimen module of a rotary type.

FIG. 7 is a side partially sectional view of a lower-specimen replaceable module of rotary type. This module in general is designated by referenced numeral 606. It consists of a mounting plate 608 with columns 610, 612, 614, and 616. The mounting plate 608 has holes 608a, 608b, . . . 608n for bolts used for attaching the module 606 to the base plate 24 of the tester. The columns 610, 612 support an electric motor 618. An output shaft 620 of the motor 618 carries a timing drive pulley 622 for an endless timing belt 624. This belt is guided over the pulley 622 and a timing driven pulley 626 attached to a driven shaft 628. This shaft passes through a seal 630 into a bowl 632. The end of the shaft 628 located inside the bowl 632 has a flange 634 with a threaded hole 636 at the end face of the shaft. The flange 634 serves for supporting a lower specimen 638, which is attached to it by a bolt 641 screwed into the threaded hole 636. If necessary to conduct tribological tests in oil, the bowl 632 can be filled with oil. Leakage of the oil from the bowl 632 is prevented due to the seal 630. If necessary, the test can be carried out with heating, i.e., at an elevated temperature. For this purpose the bowl is equipped with a cylindrical heating element 625 surrounded by a heat-insulating material 637. A thermocouple 639 is intended for measuring temperature in the bowl 632. The bowl 632 is covered with a cover 640, which has a radial slot 642 to allow radial movement of the upper specimen 283 due to horizontal displacements of the slide 46 in the guide slot 44 for adjusting position of the upper specimen 283 prior to the test.

Figure 8:
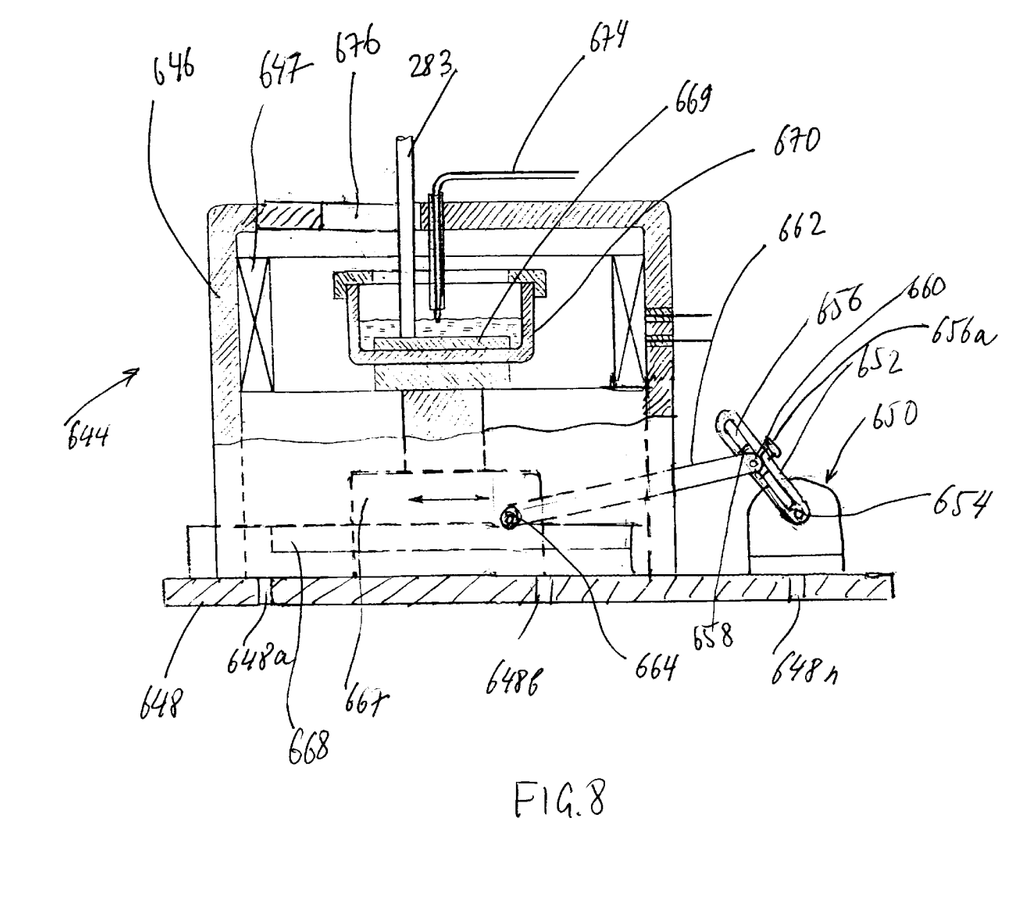
FIG. 8 is a view of an interchangeable lower-specimen module of a reciprocating type.

FIG. 8 is a schematic side sectional view of a replaceable low-specimen module with reciprocating movement of the low specimen. The module as a whole is designated by reference numeral 644. It has a rectangular box-like housing 646 installed on a mounting plate 648 which has holes 648a, 648b, . . . 648n. These holes have the same diameter and arrangement as holes 608a, 608b, . . . 608n of the mounting plate 668 shown in FIG. 7.

The mounting plate 648 supports an electric motor 650. A crank 652 is attached to an output shaft 654 of the motor 650 and radially projects therefrom. The crank has a longitudinal slot 656 with a slide block 658 slidingly guided in the slot 656. The slide block 658 has a pivot 660, which pivotally supports one end of a connecting rod 662. The opposite end of the connecting rod 662 is pivotally connected via a pivot 664 with a slider 667 guided along a guide 668 on the mounting plate 648. The slide 667 supports a cup-shaped housing 670 with a lower specimen 669 attached thereto, e.g., by bolts (not shown). Position of the slide block 658 in the slot and thus the working radius of the crank can be adjusted by moving the block 658 in the slot 656 and fixing it by a bolt 656a. Thus, rotation of the motor 650 causes, via the crank 652 and connecting rod 662, reciprocations of the slide 667. If necessary, the interior of the housing 670 can be filled with oil. The housing 670 is equipped with a heater 647 insulated with a heat-insulating material of the housing 646 and with a thermocouple 674 for measuring temperature within the housing 670. A slot 676 is provided in the upper wall of the housing 646 for adjusting position of the upper specimen 283 due to horizontal displacements of the slide 46 in the guide slot 44 for adjusting position of the upper specimen 283 prior to the test.

Figure 9:
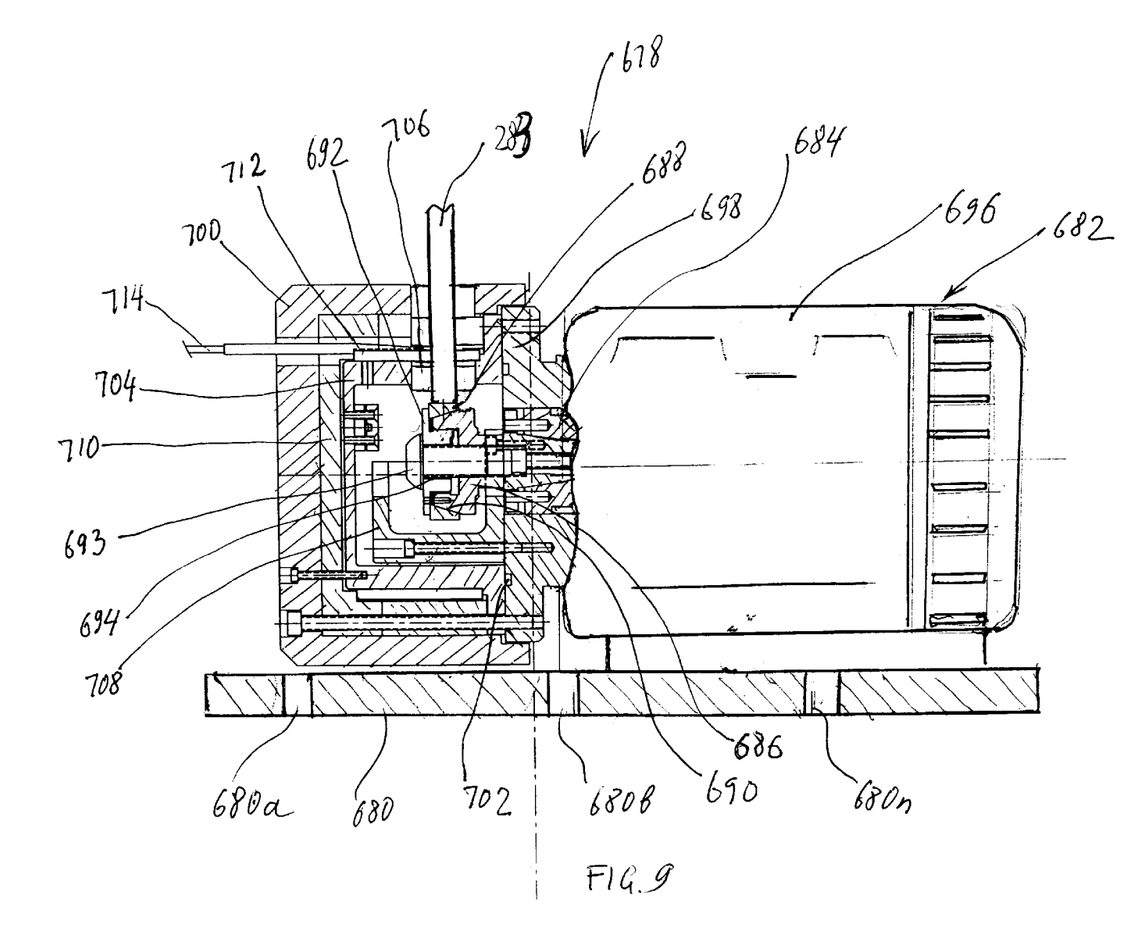
FIG. 9 is a view of an interchangeable lower-specimen module of a block-on-ring type.

FIG. 9 is a sectional view of a block-on-ring module used in the tester of the present invention. The term "block-on-ring" relates to the type of friction test where a stationary upper specimen is maintained in contact under pressure with the cylindrical peripheral surface of a rotating cylindrical lower specimen. This module, which in general is designated by reference numeral 678, has a mounting plate 680 of the same configuration and with the same holes 680a, 680b, . . . 680n as the holes 650a, 650b, . . . etc., of the previous embodiments.

The mounting plate 680 supports an electric motor 682. An output shaft 684 of the electric motor 682 supports an adapter 686 with a conical outer surface for supporting a cylindrical lower specimen 688 with a conical central opening 690. The lower specimen 688 is held in place by means of a thrust ring 692 and a bolt 693 screwed into the central threaded opening 694 on the end face of the output shaft 684. A housing 696 of the motor 682 has a flange 698 on its front end. Attached to the flange 698 is a cup-shaped outer bowl 700. Connection between the bowl 700 and the flange 698 is sealed by means of a seal ring 702. The lower specimen 688 is surrounded by an inner cup shaped bowl 704 which also is attached to the flange 698 and has a slot 706 on the upper side of the peripheral wall of the inner bowl for access of the upper specimen 283 to the lower specimen 688. Located inside the inner bowl 704 is a box-like oil holder 708. When the oil holder 708 is filled with oil, the lower peripheral portion of the lower specimen 688 is immersed into the oil bath. A space between the outer bowl 700 and the inner bowl 704 is filled with a heat-insulating material 710, and the outer surface of the inner bowl 704 is surrounded with a cylindrical heating element 712. Reference numeral 714 designates a thermocouple for measuring temperature near the zone of contact between the specimens during the test.

Operation of the Tester of the Invention

Prior to testing tribological properties of the chosen materials, or a chosen pair of materials, an upper specimen 283 is fixed in a chuck 284 (FIG. 4). An appropriate replaceable module, such as the modules 606, 644, 678 (FIGS. 7, 8, 9), or a module of any other type with a self-contained drive unit, is selected for the test and is loaded with an appropriate lower specimen, such as the specimens 638, 667, 688 (FIGS. 7, 8, 9), or a specimens of any other type required for testing. If necessary, the specimen-containing bowl or oil-holder is filled with selected oil. The module is fixed to the base plate 24 of the tester (FIGS. 2 and 3). The upper specimen 283 is position with respect to the lower specimen and is brought into contact therewith by manipulating with the carriage 30 and the slider 46 via their appropriate electric motors 26 and 34, respectively. If necessary, a temperature required for testing can be generated in the vicinity of the lower specimen by means of the heating elements, such as heating elements 634, 672, 712 (FIGS. 7, 8, 9). The lower specimen is brought into motion, which, depending on the type of the replaceable module, can be a rotary or a reciprocating motion.

Let us consider just for example that the lower specimen 638 participates in rotation and that a loading force $F_x$ is applied to the sensor assembly from the loading unit (not shown) of the tester via the stationary upper plate 104 (FIG. 4). Strictly speaking, the upper specimen is not stationary, as it moves together with the carriage and slightly together with the lower plate 102 when the beams of the sensors deform. However, for the sake of simplicity these movements of the upper specimen 283 are not taken into consideration and in the context of the present patent application the upper specimen 283 is considered as stationary.

More specifically, when the upper specimen 283 comes into contact with the moving lower specimen, application of force $F_x$ causes interaction between the upper specimen 283 and the lower specimen. The aforementioned interaction generates a reaction force $F_R$ and a friction force $F_{FR}$. These forces deform the beams 312 and 212 of both sensors and hence the strain gauges. Since the sensors are sandwiched between the upper plate 104 and the lower plate 102 and are attached to both plates in manner shown and described in connection with FIG. 4, both sensors are subject to simultaneous equal deformations in two opposite directions for eliminating misbalance created in the measurement system when a single sensor is used. Each sensor deforms in the direction of axis X under the effect of a loading force $F_x$ measured in each sensor by two strain gauges located on opposite sides of the beam near one end of the beam and in direction of axis Y under the effect of a friction force measured in each sensor by another two strain gauges located on opposite sides of the beam, which are perpendicular to the sides of strain gauges for the loading force. Since both sensors 200 and 300 are sandwiched between two plates in diagonally symmetrical positions, they transmit forces between both plates and at the same time ensure limited freedom of movement between the plates to allow deformations caused by the applied forces.

Figure 10:
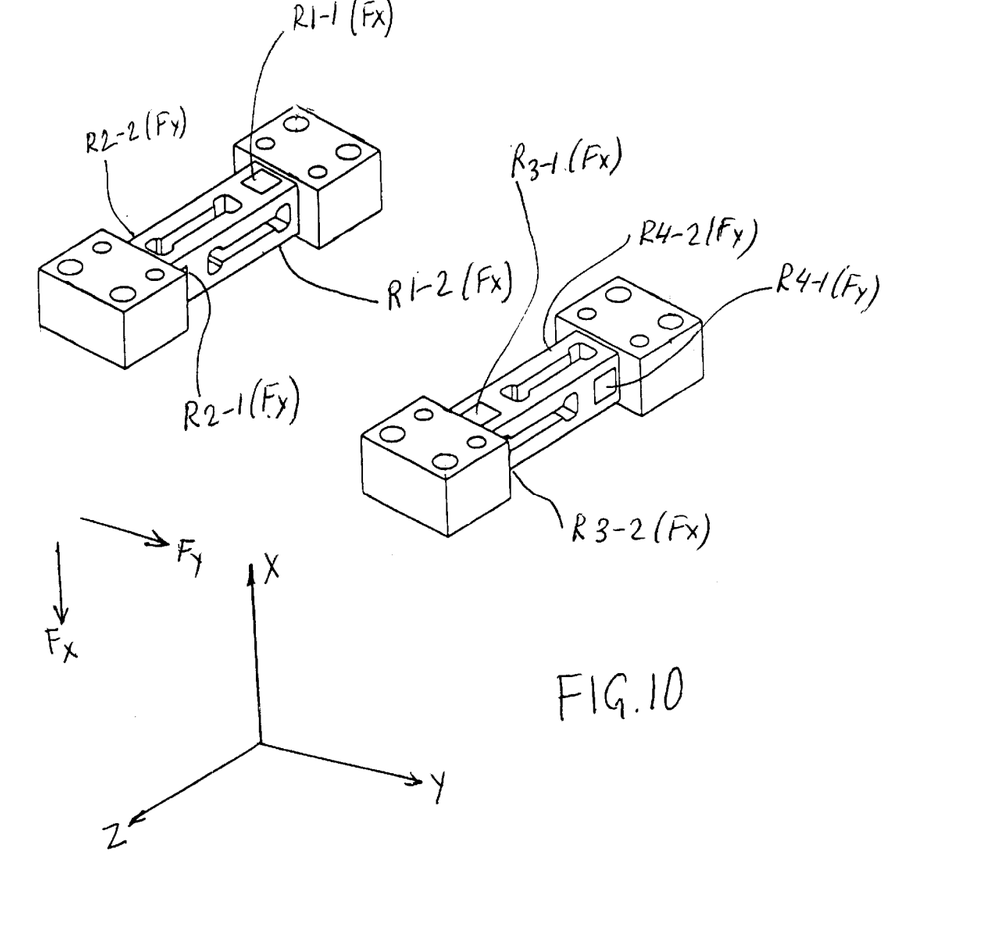
FIG. 10 is an exploded view illustrating both sensors in connection with forces applied to the sensors and measured by various strain gauges of both sensors.

Due to the provision of the slots 218 and 220 with notches 222, 224 and 226, 228, respectively, in the sensor 200 and of the slots 318 and 320 with notches 322, 324 and 326, 328, respectively, in the sensor 300, the beams 212 and 312 are deformed under effect of force $F_x$ in a X-Z plane as a first parallelograms so that the materials of the beams are stretched on the sides of the resistors R1-1 and R3-1 and are compressed on the sides of the resistors R1-2 and R3-2 (FIG. 10).

Friction force $F_{FR}$ acts in the direction of axis Y and deforms the beams 212 and 312 as second parallelograms in Z-Y plane so that the materials of the beams are stretched on the sides of resistors R2-1 and R4-1 and are compressed on the sides of resistors R2-2 and R4-2 (FIG. 10).

As the beams deform, the strain gauges also deform. These deformations change resistances of the resistors in the aforementioned bridges of the electric circuit shown in FIG. 6. As a result, resistors R1-1, R1-2 and R3-1, R3-2 measure force $F_x$, whereas resistors R2-1, R2-2 and R4-1, R4-2 measure force $F_y$.

Due to the fact that each bridge is formed by pairs of resistors one of which always increases in its resistance while the other decreases, or vice verse, the electric circuit shown in FIG. 6 improves sensitivity of the measurement system approximately by a factor of 2. Furthermore, output signals which correspond to one and the same force, e.g., force $F_x$, also are summed to form an electric signal of a doubled magnitude. Thus, increased electric signals corresponding to respective forces are supplied to the measuring and registering system (not shown).

The principle of operation described above are equally applicable to modules of other types, such the reciprocating module 644, the block-on ring module 678, or the like. The test can be carried out without heating, with heating, without oil, with oil, with the selection of different material pairs participating in friction, as well as with the selection of different oils.

The invention has been shown and described with reference to specific embodiment, which should be construed only as an example and do not limit the scope of practical applications of the invention. Therefore any changes and modifications in materials, shapes, electric diagrams and their components are possible provided these changes and modifications do not depart from the scope of the patent claims. For example, the electric bridge circuits shown in FIG. 6 can be circuits operating on a.c. current or on d.c. current. The a.c. bridge can be a resonance type bridge circuit. The strain gauge resistors can be represented by a part of a potentiometric circuit. The resistor-type strain gauges can be replaced by capacitive-type strain gauges. The sensing elements of such type can be a part of a dilatometric measurement circuit in which deformation of the gauge proportionally changes capacity of the sensing element. Although the sensors were mentioned for use in measuring a load force and a friction force, it is understood that they can be used for other purposes, such as measuring bending moments in two directions. In association with known masses properly attached to the sensors, the latter can be used as acceleration and velocity sensors. The solid end blocks 214, 216 and 314, 316 can be fixed and attached to fixation and actuating elements in a variety of modes. The beams may have an elliptical, or any other cross-section and the direction of applied forces may not necessarily be mutually perpendicular. The slots and notches may have shapes different from those shown in the drawings. The beams themselves can be assembled from several parts. The beams can be formed without notches, i.e., only with two pairs of slots. The deformable beams not necessarily should be solid bodies with the notches and slots and can be formed by four or more deformable rods, plates, or tubes which together may form two mutually perpendicular parallelograms. The strain gauges contained in one bridge circuit may have any other suitable location, e.g., on the same side of the beam instead of opposite sides of the beam.

What is claimed is:

1. An apparatus for measuring friction and wear characteristics of materials comprising:
    a frame which has a base plate, at least one vertical column, and a cross bar;
    a carriage slidingly mounted on said at least one vertical column;
    a first drive means for moving said carriage along said at least one vertical column with respect to said base plate;
    a slide slidingly mounted on said carriage in a direction parallel to said base plate;
    a second drive means for moving said slide in said direction;
    bidirectional force measurement means attached to said slide;
    a first specimen attachment means supported by said bidirectional force measurement means; and
    a replaceable module which is attachable to said base plate and has a self-contained drive means for moving a second specimen with respect to said first specimen while maintaining them in contact.

2. The apparatus of claim 1, wherein said self-contained driver means comprises a drive motor, a second specimen holder, and a transmission unit between said drive motor and said second specimen holder.

3. The apparatus of claim 2, wherein said transmission unit is selected from a rotary type transmission unit which imparts rotary motion to said second specimen holder and a reciprocating type unit which imparts reciprocating motion to said second specimen holder.

4. The apparatus of claim 3, wherein said first specimen has a longitudinal axis, said rotary type transmission unit has an axis of rotation and is selected from a group consisting of a rotary drive unit with said axis of rotation parallel to said longitudinal axis and perpendicular to said longitudinal axis.

5. The apparatus of claim 3, wherein said replaceable module further comprises heating means for testing said first and second specimens under heating conditions.

6. The apparatus of claim 5, wherein said replaceable module further comprises lubricating means for testing said first and second specimens under lubrication conditions.

7. The apparatus of claim 3, wherein said replaceable module further comprises lubricating means for testing said first and second specimens under lubrication conditions.

8. The apparatus of claim 1, wherein said bidirectional force measurement means comprises a device for measuring a first force acting in one direction and a second force acting in a direction which is different from said one direction and is not parallel thereto, said device comprising:
    a first mounting member;
    a second mounting member;
    a first flexible member, one end of which is attached to said first mounting member and the opposite end is attached to said second mounting member;
    a second flexible member, which is identical to said first flexible member, is arranged parallel thereto and has one end, which corresponds to said one end of said first flexible member, attached to said second mounting member, and the opposite end, which corresponds to said opposite end of said first flexible member, attached to said first mounting member; and
    deformation sensitive means for measuring deformations of said first flexible member and of said second flexible member in terms of said first force and said second force respectively, said first flexible member and said second flexible member being deformed simultaneously by equal amounts and in mutually opposite directions.

9. The apparatus of claim 8, wherein said first force is a loading force, said second force is a friction force, said first mounting member is a first plate, said second mounting member is a second plate, said first flexible member and said second flexible member comprising deformable beams sandwiched between said first plate and said second plate.

10. The apparatus of claim 9, wherein each of said deformable beams comprises:
    a first pair of deformable portions for deforming said deformable beam in said one direction and a second pair of deformable portions for deforming said deformable beam in said direction which is different from said one direction;
    a first pair of deformation sensitive elements attached to opposite sides of one of said deformable portions of said first pair and a second pair of deformation sensitive elements attached to opposite sides of one of said deformable portions of said second pair;
    said first pair of deformable portions and said second pair of deformable portions being formed in said deformable beam by a first pair of through holes with a first through slot which interconnects said first pair of through holes, said first pair of through holes and said first through slot passing through said deformable beam in said direction different from said one direction, and by a second pair of through holes with a second through slot which interconnects said second pair of said through holes, said second through holes and said second through slot passing through said deformable beam in said one direction; each through hole of said first pair of through holes and of said second pair of through holes having a longitudinal axis;

said first pair of said through holes comprising a first through hole located close to one end of said deformable beam and having its respective longitudinal axis in said direction different from said one direction and a second through hole located close to the end of said deformable beam opposite to said one end and having its respective longitudinal axis in said direction different from said one direction;

said second pair of said through holes comprising a third through hole located close to one end of said deformable beam and having its respective longitudinal axis in said one direction and a fourth through hole located close to the end of said deformable beam opposite to said one end and having its respective longitudinal axis in said one direction;

said second through hole and said third through hole being located between said first through hole and said fourth through hole;

said second through hole being located between said third through hole and said fourth through hole;

said third through hole being located between said first through hole and said second through hole.

11. The apparatus of claim 10, wherein each of said deformable beams further comprises a first beam attachment means connected to said one end of said deformable beam and a-second attachment means connected to said end opposite to said one end.

12. The apparatus of claims 8, wherein each of said deformation sensitive means comprises a strain gauge.

13. The apparatus of claim 10, wherein each of said deformation sensitive elements comprises a strain gauge.

14. The apparatus of claim 8, wherein said one direction and said direction different from said one direction are mutually perpendicular directions.

15. The apparatus of claim 8, wherein each of said flexible members has a longitudinal axis and comprises: a first parallelogram deformable in the direction of said one force; a second parallelogram deformable in said direction different from said one direction, said first parallelogram being at least partially overlapped with said second parallelogram in the direction of said longitudinal axis;

said first parallelogram being formed at least by a first through slot passing through said flexible member in said direction different from said one direction, and said second parallelogram is formed at least by a second through slot passing through said flexible member in said one direction.

16. The apparatus of claim 15, wherein each of said flexible members further comprises a first pair of through notches which are wider than said first slot and which are connected to both ends of said first slot and a second pair of through notches which are wider than said second slot and which are connected to both ends of said second slot.

17. The apparatus of claim 15, wherein in each of said flexible members said deformation sensitive means comprise:

a first pair of strain gauges located at one end of said first through slot and on opposite sides of said first parallelogram for measuring said one force; and a second pair of strain gauges located at the end of said second through slot opposite to said one end and on the opposite sides of said second parallelogram for measuring said second force.

18. The apparatus of claim 17, further comprising an electric circuit, wherein in each of said flexible members said first pair of strain gauges forms a first bridge for measuring. said first force, whereas said second pair of strain gauges forms a second bridge for measuring said second force.

19. A method for measuring friction and wear characteristics of materials, comprising:

providing a tester having means for stationary supporting a first specimen, means for moveably supporting a second specimen located beneath said first specimen, means for bringing said first specimen in contact with said second specimen and for application of a loading force to said first specimen when said second specimen is moving, and bidirectional force measurement means for measuring said loading force and a friction force that occurs in said contact;

attaching said first specimen to means for stationary supporting said first specimen;

causing movement of said second specimen;

bringing said first specimen in contact with said second specimen;

applying said loading force to said first specimen which it is moving;

simultaneously measuring said loading force and-said friction force with said bidirectional force measurement means;

providing said bidirectional force measurement means with a first plate, a second plate, a first deformable member and a second deformable member sandwiched between said first plate and said second plate in a diagonally symmetrical positions with respect to each other so that one end of each of said deformable members is attached to one of said plates and the opposite end to the other of said plates;

providing each of said deformable members with first measuring means for measuring said loading force and with second measurement means for measuring said friction force;

applying said loading force to said first plate and said friction force to said second plate; and measuring said loading force and said friction force simultaneously in both of said deformable members.

20. The method of claim 19, comprising:

forming each of said deformable members in the form of a first deformable parallelogram deformable under the effect of said loading force in said one direction and a second deformable parallelogram deformable under the effect of said friction force in said second direction, said first deformable parallelogram and said second deformable parallelogram being at-least partially-overlapped.

* * * * *